(12) United States Patent
Ho et al.

(10) Patent No.: US 9,387,301 B2
(45) Date of Patent: Jul. 12, 2016

(54) PAD ASSEMBLY HAVING OUTER CASING AND SUPPORT ELEMENT

(75) Inventors: Peter Cha Fi Ho, Pittsburgh, PA (US); Lance Ranard Busch, Trafford, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 487 days.

(21) Appl. No.: 13/451,799

(22) Filed: Apr. 20, 2012

(65) Prior Publication Data

US 2012/0199132 A1 Aug. 9, 2012

Related U.S. Application Data

(63) Continuation-in-part of application No. 11/642,024, filed on Dec. 19, 2006, now Pat. No. 7,743,768.

(51) Int. Cl.
 *A62B 18/02* (2006.01)
 *A62B 18/08* (2006.01)
 *A61M 16/06* (2006.01)

(52) U.S. Cl.
 CPC ............ *A61M 16/06* (2013.01); *A61M 16/0633* (2014.02); *A61M 16/0655* (2014.02); *Y10T 29/49826* (2015.01)

(58) Field of Classification Search
 CPC .................. A61M 16/0605; A61M 16/0633; A61M 16/0655; A61M 2016/0661
 USPC ............. 128/205.25, 206.21, 206.24, 207.11, 128/206.28, 207.13
 See application file for complete search history.

(56) References Cited

U.S. PATENT DOCUMENTS

| | | | |
|---|---|---|---|
| 2,047,216 A | 7/1936 | McKesson |
| 2,749,910 A | 6/1956 | Faulconer, Jr. |
| 2,875,757 A | 3/1959 | Galleher |
| 2,877,764 A | 3/1959 | Galleher |
| 2,931,356 A | 4/1960 | Hermann |
| 3,330,274 A | 7/1967 | Bennett, V |
| 4,799,477 A | 1/1989 | Lewis |
| 4,811,730 A | 3/1989 | Milano |
| 4,873,972 A | 10/1989 | Magidson |
| 4,907,584 A | 3/1990 | McGinnis |
| 4,915,105 A | 4/1990 | Lee |
| 4,971,051 A | 11/1990 | Toffolon |
| 5,121,745 A | 6/1992 | Israel |
| 5,243,971 A | 9/1993 | Sullivan |
| 5,349,949 A | 9/1994 | Schegerin |
| 5,428,844 A | 7/1995 | Dougherty |
| 5,517,986 A | 5/1996 | Starr |

(Continued)

FOREIGN PATENT DOCUMENTS

| | | |
|---|---|---|
| DE | 3535045 A1 | 4/1987 |
| DE | 102005033649 A1 | 1/2007 |

(Continued)

*Primary Examiner* — Kristen Matter
(74) *Attorney, Agent, or Firm* — Michael W. Haas

(57) ABSTRACT

A pad assembly for use with a gas delivery mask for delivering a flow of gas to an airway of a patient is described. The pad assembly includes an outer casing and a support element. The outer cashing has a housing portion and a mounting portion. The housing portion has a first wall and a second wall defining a hollow cavity therebetween. The first wall is structured to engage a portion of the patient, and the mounting portion is structured to couple the outer casing to the patient interface device. The support element is disposed substantially within the cavity of the outer casing.

13 Claims, 7 Drawing Sheets

(56) References Cited

U.S. PATENT DOCUMENTS

| | | |
|---|---|---|
| 5,570,689 A | 11/1996 | Starr |
| 5,592,938 A | 1/1997 | Scarberry |
| 5,627,611 A | 5/1997 | Scheiner |
| 5,647,357 A | 7/1997 | Barnett |
| 5,884,624 A | 3/1999 | Barnett |
| 6,112,746 A | 9/2000 | Kwok |
| 6,119,693 A | 9/2000 | Kwok |
| 6,119,694 A | 9/2000 | Correa |
| 6,357,441 B1 | 3/2002 | Kwok |
| 6,397,847 B1 | 6/2002 | Scarberry |
| 6,408,853 B1 | 6/2002 | Chang |
| 6,409,954 B1 | 6/2002 | Mulligan |
| 6,467,482 B1 | 10/2002 | Boussignac |
| 6,467,483 B1* | 10/2002 | Kopacko et al. ......... 128/207.12 |
| 6,494,206 B1 | 12/2002 | Bergamaschi |
| 6,615,832 B1 | 9/2003 | Chen |
| 6,631,718 B1 | 10/2003 | Lovell |
| 6,641,264 B1 | 11/2003 | Schwebel |
| 6,651,661 B2 | 11/2003 | Matioc |
| 6,679,260 B2 | 1/2004 | Her |
| 6,718,979 B1 | 4/2004 | Britt |
| 6,834,650 B1 | 12/2004 | Fini |
| 6,843,249 B2 | 1/2005 | Bergamaschi |
| 6,895,965 B2 | 5/2005 | Scarberry |
| 7,231,922 B2 | 6/2007 | Davison |
| 7,243,652 B2 | 7/2007 | Chang |
| 7,278,428 B2 | 10/2007 | Fini |
| 8,051,855 B2 | 11/2011 | Ho |
| 2002/0029780 A1 | 3/2002 | Frater |
| 2003/0075181 A1 | 4/2003 | Bergamaschi |
| 2003/0084904 A1* | 5/2003 | Gunaratnam ............ 128/206.27 |
| 2004/0007231 A1 | 1/2004 | Zhou |
| 2004/0025883 A1 | 2/2004 | Eaton |
| 2004/0045551 A1 | 3/2004 | Eaton |
| 2004/0216747 A1* | 11/2004 | Jones et al. ............. 128/206.21 |
| 2004/0221227 A1 | 11/2004 | Wu |
| 2005/0072428 A1 | 4/2005 | Ho |
| 2005/0092327 A1 | 5/2005 | Fini |
| 2006/0081251 A1 | 4/2006 | Hernandez |
| 2006/0157064 A1 | 7/2006 | Davison |
| 2006/0174890 A1 | 8/2006 | Cheng |
| 2006/0185675 A1 | 8/2006 | Colin |
| 2006/0249159 A1 | 11/2006 | Ho |
| 2007/0107733 A1 | 5/2007 | Ho |
| 2007/0125385 A1 | 6/2007 | Ho |
| 2007/0163594 A1 | 7/2007 | Ho |
| 2007/0221226 A1 | 9/2007 | Hansen |
| 2007/0221227 A1* | 9/2007 | Ho ............................ 128/206.24 |
| 2008/0006277 A1 | 1/2008 | Worboys |
| 2008/0257354 A1 | 10/2008 | Davidson |
| 2008/0289633 A1 | 11/2008 | Kwok |
| 2009/0014007 A1* | 1/2009 | Brambilla et al. ....... 128/206.24 |

FOREIGN PATENT DOCUMENTS

| | | |
|---|---|---|
| DE | 202008008244 U1 | 6/2008 |
| DE | 102007022639 A1 | 11/2008 |
| EP | 1205205 A2 | 5/2002 |
| JP | 55-092339 U | 6/1980 |
| WO | WO03105921 A2 | 12/2003 |

\* cited by examiner

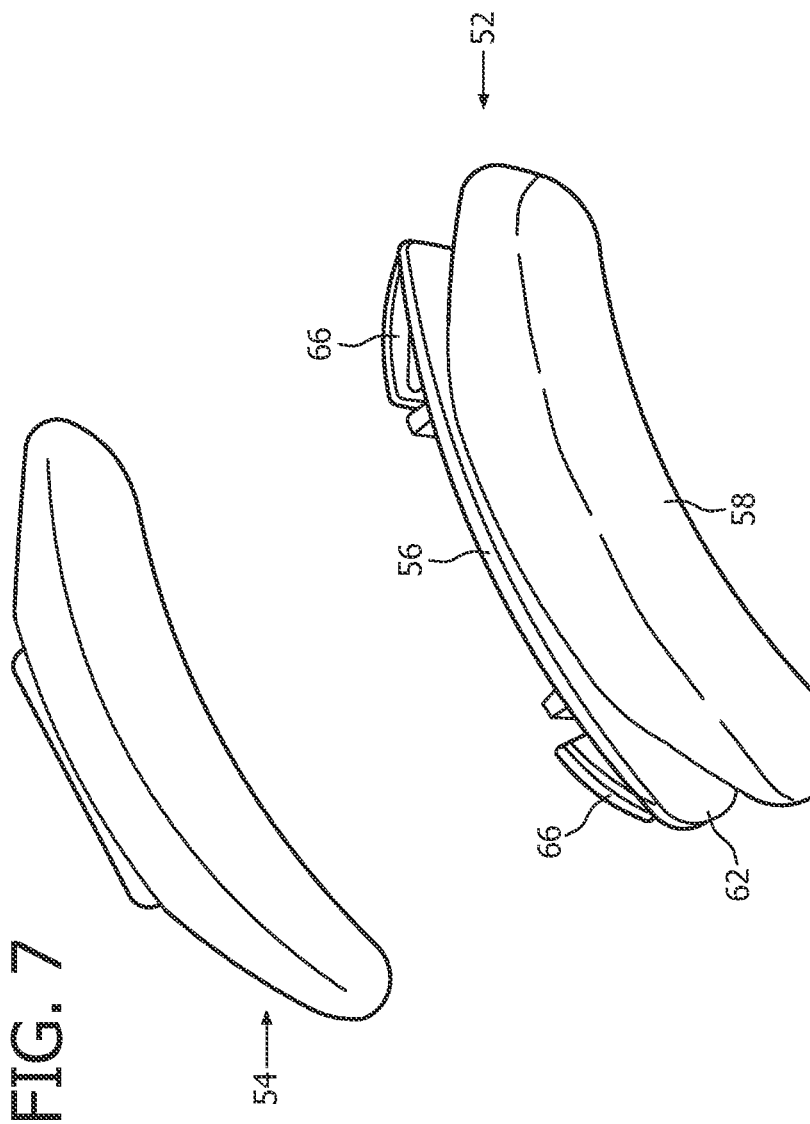

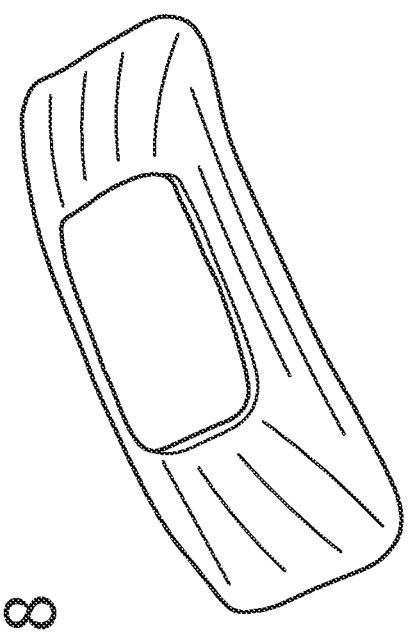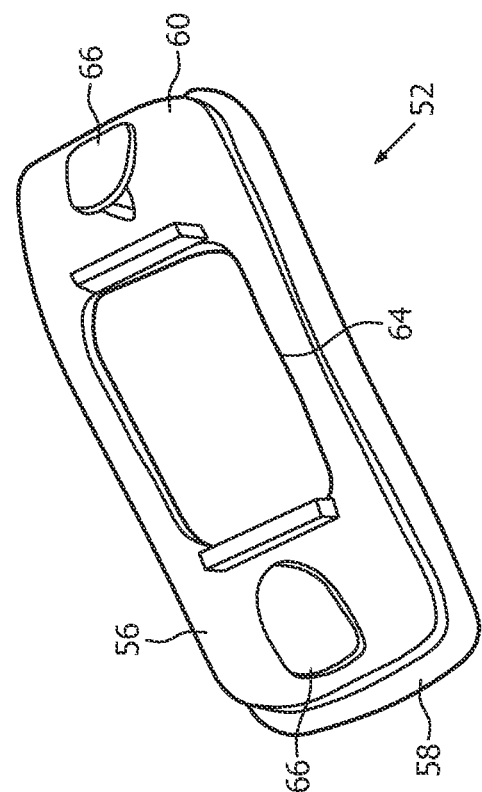

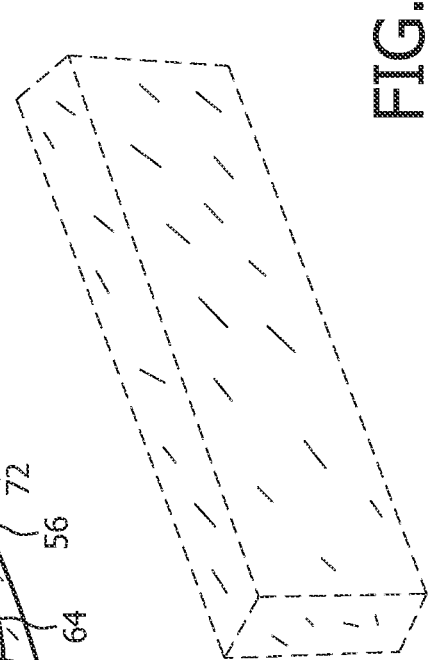
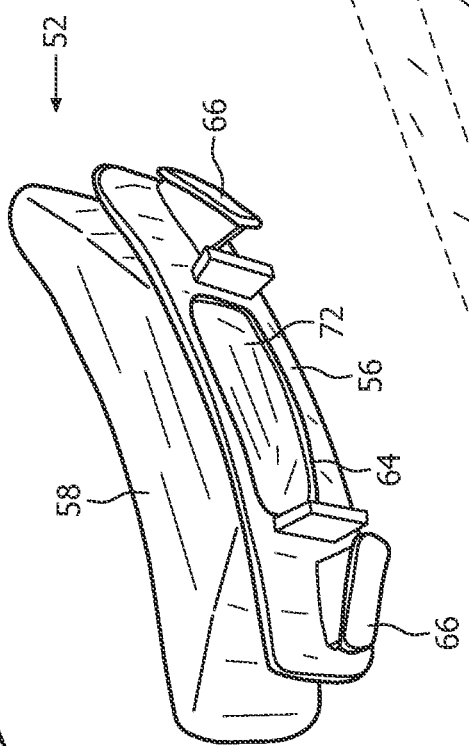
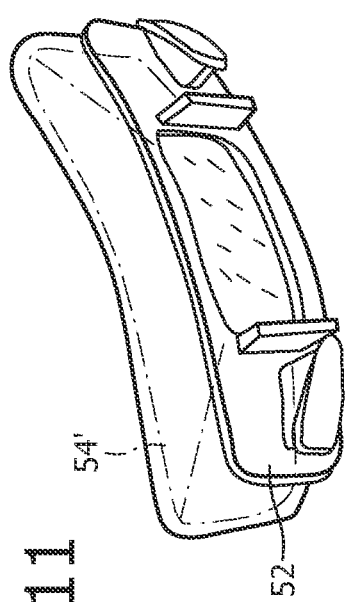

PAD ASSEMBLY HAVING OUTER CASING AND SUPPORT ELEMENT

CROSS-REFERENCE TO RELATED APPLICATIONS

This patent application is a Continuation-In-Part under 35 U.S.C. §120 of U.S. patent application Ser. No. 11/642,024, filed Dec. 19, 2006, now U.S. Pat. No. 7,743,768, granted Jun. 29, 2010, the contents of which are herein incorporated by reference.

BACKGROUND OF THE INVENTION

1. Field of the Invention

The present invention pertains to a foam insert filled pad for use with a support system for a patient interface device, and, in particular to a forehead support system for a patient interface device for supplying a flow of gas to a patient. The invention further pertains to a gas delivery system that incorporates such a forehead support system using such a foam insert filled pad.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation (NIV). It is also known to deliver continuous positive airway pressure (CPAP) or variable airway pressure, such as a bi-level pressure that varies with the patient's respiratory cycle or an auto-titrating pressure that varies with the monitored condition of the patient. Typical pressure support therapies are provided to treat a medical disorder, such as sleep apnea syndrome, in particular, obstructive sleep apnea (OSA), chronic obstructive pulmonary disease (COPD), or congestive heart failure (CHF).

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient. It is known to maintain such masks on the face of a patient by a headgear having upper and lower straps, each having opposite ends threaded through connecting elements provided on the opposite sides and top of a mask.

Because such masks are typically worn for an extended period of time, it is important the headgear maintain the mask in a tight enough seal against a patient's face without discomfort. A problem arises in that in order for the mask to maintain a seal without any undue gas leaks around the periphery of the mask, the mask may be compressed against the patient's face and thus be uncomfortable to the patient.

It is known to provide forehead supports associated with patient interface devices to provide a support mechanism between the mask and the patient's forehead. Patient interface devices having forehead cushions, spacers, or supports are described in U.S. Pat. Nos. 4,907,584; 5,243,971; 5,517,986; 5,570,689; 6,119,693 and 6,357,441. The forehead supports prevent the mask from exerting too much force on a patient's face at one general location by dispersing the load over a larger area, provide greater control of the force on the patient at certain pressure points, such as at the bridge of the nose, and provide stability to the mask.

Although these conventional patient interface devices have advanced the art, the need still exists for a patient interface device that improves upon existing devices, for example, to maximize patient comfort while minimizing leak, during delivery of a positive airway pressure or flow of gas to the airway of the user. For example, many conventional patient interface devices tend to focus on minimizing the area of a patient's face to which strapping forces are applied. As such, a need exists for improved pad designs for use in such applications.

SUMMARY OF THE INVENTION

Accordingly, it is an object of the present invention to provide an improved patient interface device that overcomes the shortcomings of conventional patient interface devices. This object is achieved according to one embodiment of the present invention by providing a pad assembly for use with a patient interface device in delivering a flow of gas to an airway of a patient is provided. The pad assembly includes an outer casing having a housing portion and a mounting portion. The housing portion includes a first wall and a second wall defining a hollow cavity therebetween. The first wall is structured to engage a portion of the patient and the mounting portion is structured to couple the outer casing to the patient interface device. The pad assembly further includes a support element disposed substantially within the cavity of the outer casing.

Another embodiment of the present invention provides a patient interface device including a mask shell, a seal member, and a support having a pad assembly. The mask shell having a patient side and an outer side opposite the patient side adapted for receiving a flow of gas. The seal member having a first end portion adapted to contact a first area of a patient's face to form a seal therewith and a second end portion opposite the first end portion, the second end portion coupled to the mask shell. The support member coupled to the mask shell. The pad assembly including an outer casing having a housing portion and a mounting portion. The housing portion having a first wall and a second wall defining a hollow cavity therebetween. The first wall is structured to engage a portion of the patient, and the mounting portion is structured to couple the outer casing to the support member. the pad assembly further including a support element disposed substantially within the cavity of the outer casing.

A further embodiment of the present invention provides a method of providing a customizable pad assembly for use with a patient interface device for delivering a flow of gas to an airway of a patient. The method includes providing an outer casing having a housing portion and a mounting portion. The housing portion having a first wall and a second wall defining a hollow cavity therebetween. The first wall being structured to engage a portion of the patient, and the mounting portion being structured to couple the outer casing to the patient interface device. The method further including providing a plurality of support elements, each support element being disposable substantially within the cavity of the outer casing.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIGS. 4-6 and 12 are views of an outer casing of a pad assembly according to an exemplary embodiment of the present invention;

FIGS. 7 and 8 are views of a support element of a pad assembly according to an exemplary embodiment of the invention;

FIG. 10 is a view of a support element of a pad assembly according to another exemplary embodiment of the invention; and FIG. 11 is a view of a pad assembly incorporating the outer casing of FIGS. 4-6 and the support element of FIG. 10.

DETAILED DESCRIPTION OF EXEMPLARY EMBODIMENTS

Figure 1:
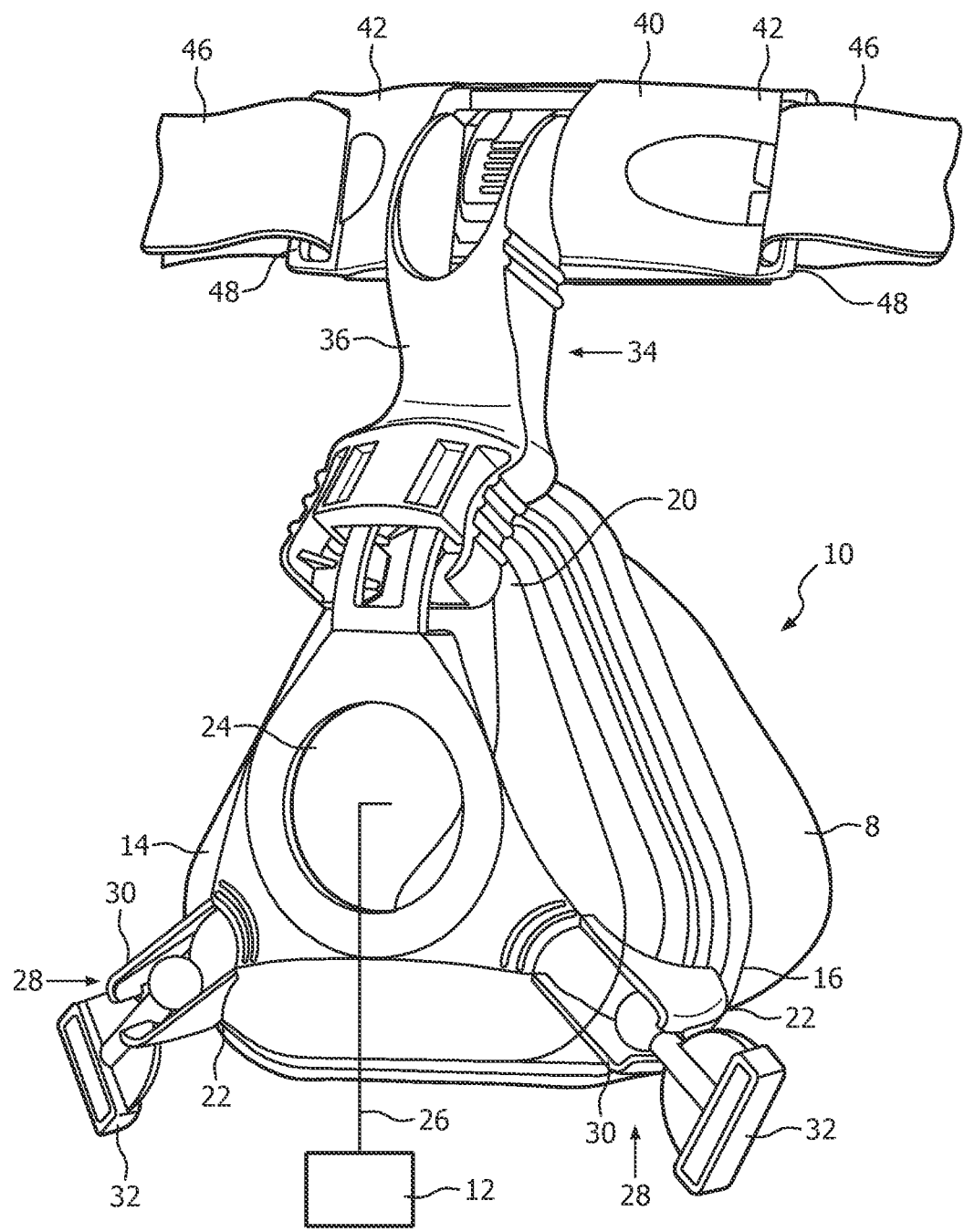
FIG. 1 is a perspective view a patient interface device that includes a forehead support system having a modular pad according to the principles of an exemplary embodiment of the present invention shown (schematically) connected to a gas flow generating device.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, the terms "fastener" and "attachment mechanism" refer to any known or suitable securing mechanisms for securing one part to another part, and expressly include, but are not limited to mechanical mechanisms, Velcro, snaps and adhesives. As employed herein, the term "number" shall mean one or an integer greater than one (i.e., a plurality).

Figure 2:
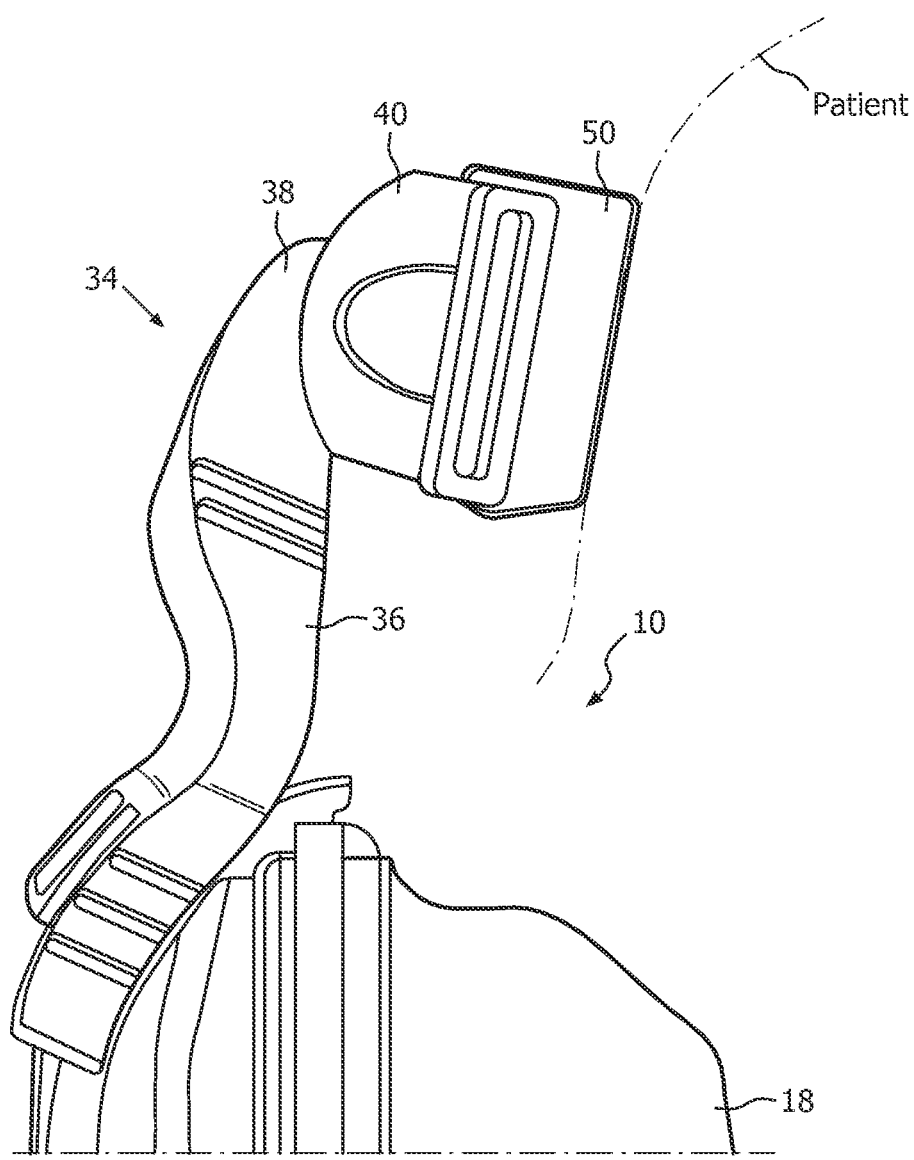
FIG. 2 is a partial side of the mask and forehead support system of FIG. 1.
Figure 3:
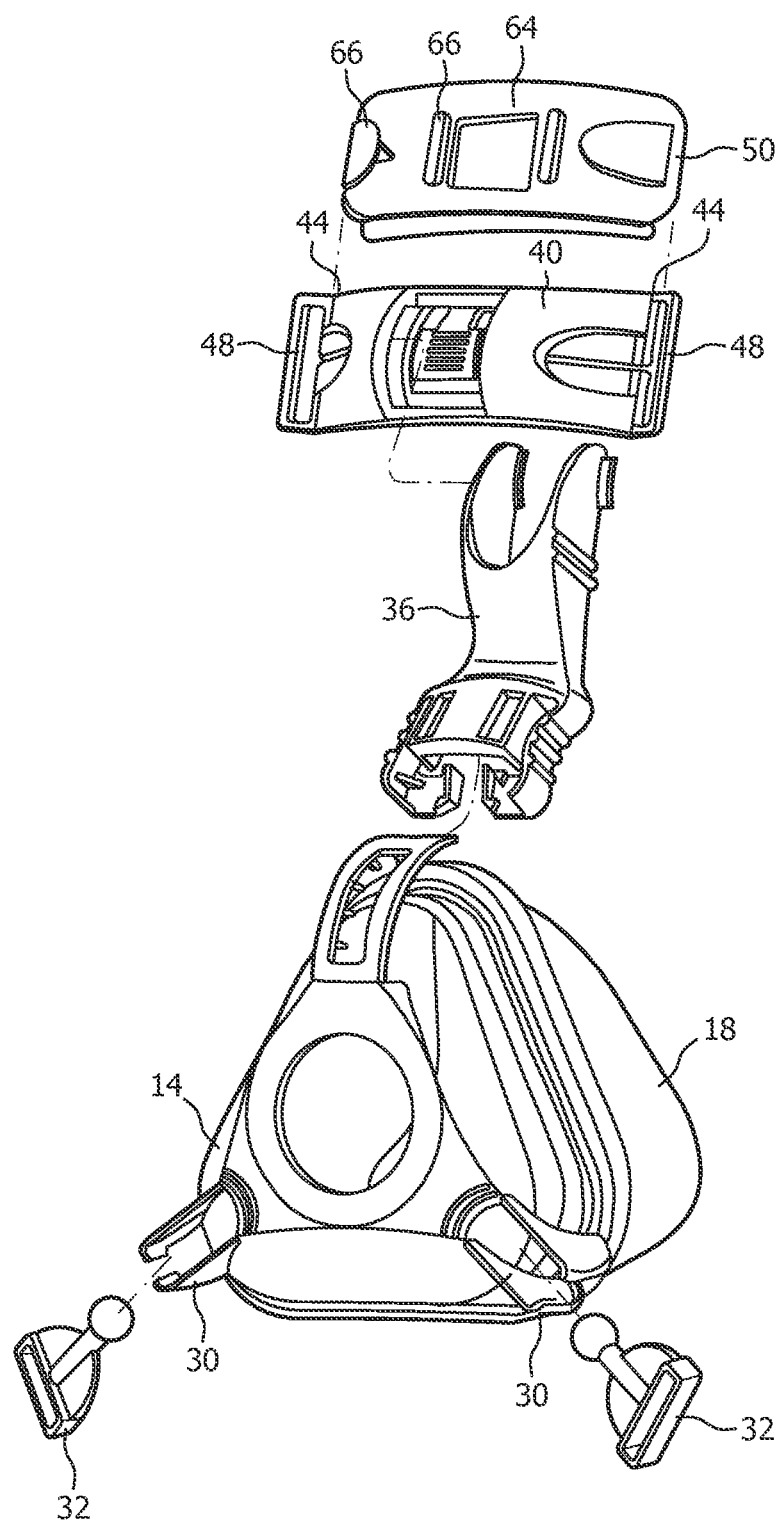
FIG. 3 is an exploded view of the mask and forehead support system of FIG. 1.

FIGS. 1-3 illustrate an exemplary embodiment of a patient interface device 10 (also referred to as a gas delivery mask) according to the principles to the present invention. Patient interface device 10 functions to communicate a flow of breathing gas between a patient's airway and a pressure generating device 12 (shown schematically), such as a ventilator, CPAP device, autotitrating CPAP device, PPAP, PAV®, or variable pressure device, e.g. a BiPAP® device manufactured and distributed by Phillips Respironics, Inc. of Pittsburgh, Pa., in which the pressure provided to the patient varies with the patient's respiratory cycle so that a higher pressure is delivered during inspiration than during expiration.

Referring to FIGS. 1-3, there is illustrated a patient interface device 10 in the form of a gas delivery mask for delivering a flow of gas to an airway of a patient. Patient interface device 10 includes a mask shell 14 or body portion, which is preferably, but not necessarily, a generally rigid, formed structural shell having an open side that defines an annular portion 16 to which a resilient, relatively soft cushion or seal member 18 is attached.

In the illustrated exemplary embodiment, mask shell 14 is substantially triangular in shape, having an upper apex angle 20 and two lower angles 22. Mask shell 14 includes an inlet opening 24 adapted to receive a gas supply conduit 26 (shown schematically). In an exemplary embodiment, mask shell 14 is formed from rigid plastic, such as Polycarbonate. Seal member 18 is configured to receive a portion of the patient, such as the nose.

The mask illustrated in FIGS. 1-3 is a typical nasal mask. It is to be appreciated that the present invention can be used on any patient interface device either nasal, oral, oral-nasal or nasal cannula system, as long as the mask employs a separate support or supports that contact any part of the face other than the sealing area. It is to further be appreciated that although the exemplary embodiment shown in the figures is a forehead pad piece, which is conventionally placed above the cushion (sealing element) on the forehead of a patient, the present invention may be employed with other external supports (e.g., without limitation, cheek pads).

In the illustrated exemplary embodiment, a lower headgear connector assembly 28 includes a pair of first connectors 30 rigidly attached to lower angles 22 of mask shell 14. Lower headgear straps (not shown) in headgear assembly are selectively connected to mask 10 by means of a second connector 32. In the illustrated embodiment, a pair of second connectors 32, are removably connectable to end portions of headgear straps (not shown) and are also removably connectable to first connectors 30 on each side of mask shell 14. Alternately, lower headgear connector assembly 28 can be any suitable headgear connector assembly.

Likewise, the present invention contemplates the headgear can be any suitable headgear, i.e., any conventional headgear used in the patient interface field. For example, a typical headgear assembly comprises a headpiece (not shown) that overlies a portion of the patient's crania and with a pair of lower headgear straps and a pair of upper headgear straps extending therefrom to adjustably connect the headgear to the mask.

A forehead support 34, according to the illustrated exemplary embodiment, is provided at upper apex angle 20. Forehead support 34 in this embodiment is generally T-shaped and includes a support arm 36, which is connected at its upper end 38 (FIG. 2) to a horizontal forehead support bracket 40. Forehead support bracket 40 includes a forehead pad assembly 50 (FIGS. 2 and 3) on the patient contacting side which is discussed in further detail below. Each end portion 42 of forehead support bracket 40 may include a connector element 44 for securing an upper headgear strap 46. In the embodiment depicted in FIGS. 1-3, connector element 44 is a female receiving slot for receiving a male quick release element 48 attached to an upper headgear strap 46. However, it should be apparent that other connection mechanisms could be used.

Pad assembly 50 forms the actual contact point of forehead support bracket 40 to the forehead of the patient (shown in phantom line in FIG. 2) and includes an outer casing 52 and a support element 54. Outer casing 52 has a generally hollow springy structure preferably formed from a rubbery material such as silicone or thermoplastic elastomer (TPE) or other suitable material, which is preferably substantially impermeable to moisture. In this manner, outer casing 52 will be relatively easy to wipe clean, and will also function to prevent the undesired entry of moisture into support element 54 contained therein, as will be described below.

In an exemplary embodiment, outer casing 52 was molded in a silicone rubber with hardness about 20 to 40 Shore A with a wall thickness from about 0.75 millimeters to about 1.5 millimeters. Referring to FIGS. 4-6 and 12, outer casing 52 includes a mounting portion 56 and a housing portion 58. Mounting portion 56 is of slightly curved shape and includes a first side 60, an opposite second side 62 and an opening 64 passing therebetween. A number of coupling mechanisms 66 extend from first side 60 of mounting portion 56 for use in coupling pad assembly 50 to forehead support bracket 40. In the exemplary embodiments shown, coupling mechanisms 66 comprise protrusions that are connectable to respective openings (not illustrated) on forehead support bracket 40.

Figure 5:
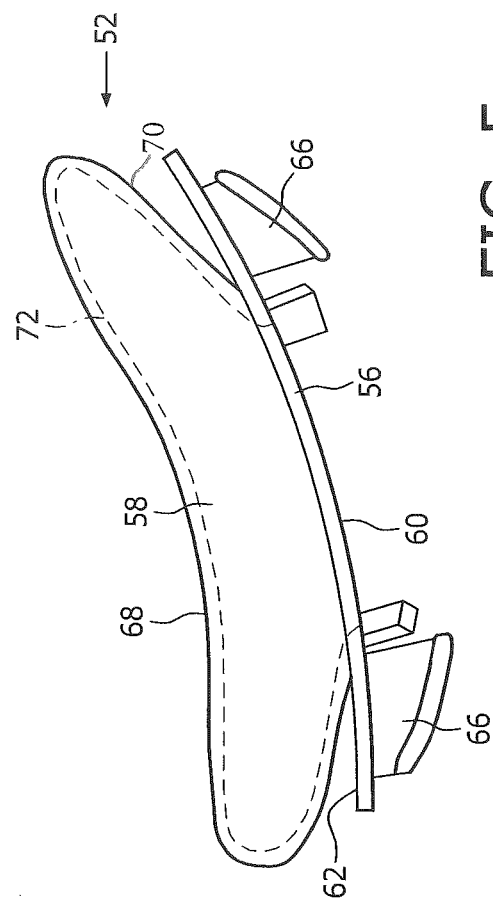

As perhaps best shown in FIG. 5, for example, housing portion 58 is formed from a slightly curved first wall 68 structured to contact the patient and a second wall 70, generally curved a greater amount than first wall 68. Second wall 70 is coupled to second side 62 thus coupling housing portion 58 and mounting portion 56 together. In the exemplary embodiment depicted, mounting portion 56 and housing portion 58 are formed as a unitary member, however it is to be appreciated that mounting portion 56 and housing portion 58 could be formed separately without varying from the scope of the present invention. First wall 68 and second wall 70 of housing portion 58 generally define a cavity 72 therebetween, as shown in hidden line drawing in FIG. 5.

Figure 9:
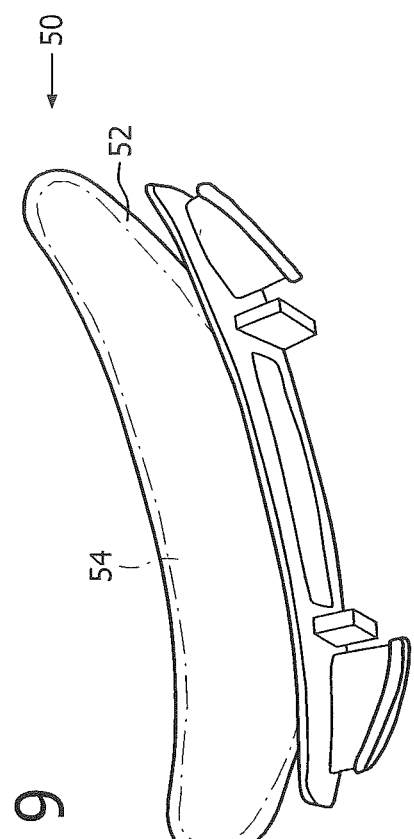
FIG. 9 is a view of a pad assembly incorporating the outer casing of FIGS. 4-6 and the support element of FIGS. 7 and 8.

FIGS. 7 and 8 show an exemplary support element 54 according to an embodiment of the invention in which support element 54 is custom formed from a "closed" cell skinned foam material, such as a silicone-foam material formed to cooperatively fit within cavity 72 of housing portion 58 of outer casing 52, as shown by phantom line in the pad assembly 50 of FIG. 9. The flexible nature of outer casing 52 and support element 54 allow for the insertion of support element 54 into outer casing 52 via opening 64. Once installed, outer casing 52 substantially surrounds support element 54. In an exemplary embodiment, a silicone-foam material having a density (pcf) of about 14.5, a softness (Shore 000) of about 20-25, and an average cell size (mm in diameter) of about 0.5 (fairly uniform ranging from about 0.2 to 0.8) in open cell structure, has been employed. In another exemplary embodiment, a polyurethane foam (either Ester or Ether) having a density (pcf) of about 8.5, a softness (Shore 000) of about 20-25, and an average cell size (mm in diameter) of about 0.5 (fairly uniform ranging from about 0.2 to 0.8) in open cell structure, has been employed.

As an alternative to the use of formed "closed" cell skinned materials for support element 54 as described above, support element 54 may also be formed from an "open" cell soft foam material such as, for example without limitation, any non structural foam with compression and expansion capability, typical materials are Polystyrene and Polyurethane. Such "open" cell foam material may be die cut, such as shown by support element 54' of FIG. 10. Alternatively, such "open" cell material may be suitably formed to have a desired shape, such as, for example without limitation, the shape of support element 54 of FIGS. 7-9. In either case, the rather soft nature of support element 54' will generally result in support element 54' contouring to the shape of cavity 72 as shown in phantom line in the pad assembly 50' of FIG. 11.

It is to be appreciated that in addition to the exemplary embodiments described herein, support element 54 may also be formed from any suitable resilient cushioning material, and may include, for example and without limitation, more than one element and/or different sizes or variations of elements formed from alternative materials, such as gel, foam, silicone, or viscoelastic foam or memory foam. Additionally, the selection of the particular material employed as support element 54 or, at minimum, particular attributes of the material, may be left up to the end user (patient) to allow for custom tailoring of the pad assembly 50 by the patient. In such instances, a number of different types of interchangeable support elements 54 would be supplied from which the patient could pick and choose as desired.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pad assembly for use with a patient interface device, the pad assembly comprising:
    an outer casing having a housing portion and a mounting portion formed as a unitary member made of a flexible material having a hardness of about 20 to 40 Shore A, the housing portion having a first wall and a second wall defining a hollow cavity therebetween, the first wall being structured to engage a portion of the patient, the mounting portion being structured to couple the outer casing to the patient interface device, the mounting portion having a first side and an opposite second side, wherein the first side and the second side form an internal edge of the mounting portion defining an opening through the mounting portion, wherein the second wall of the housing portion is directly coupled to and extends directly from the second side of the mounting portion at the internal edge, and wherein the first side of the mounting portion comprises a coupling mechanism extending therefrom in a direction away from the housing portion, the coupling mechanism being structured to couple the pad assembly to the patient interface device; and
    a support element disposed substantially within the cavity of the outer casing, wherein the opening is structured to flex and receive the support element therethrough for disposing the support element in the cavity by flexing of the mounting member.

2. The pad assembly of claim 1, wherein the first wall of the housing portion is generally curved and wherein the second wall of the housing portion is generally curved a greater amount than the first wall.

3. The pad assembly of claim 1, wherein the support element comprises an open cell foam material.

4. The pad assembly of claim 1, wherein the support element comprises a closed cell foam material.

5. The pad assembly of claim 1, wherein the outer casing is formed from a silicone or thermoplastic elastomer material.

6. A patient interface device comprising:
a mask shell having a patient side and an outer side opposite the patient side adapted for receiving a flow of gas;
a seal member having a first end portion adapted to contact a first area of a patient's face to form a seal therewith and a second end portion opposite the first end portion, the second end portion coupled to the mask shell; and
a support member coupled to the mask shell, the support member having a pad assembly comprising:
an outer casing having a housing portion and a mounting portion formed as a unitary member made of a flexible material having a hardness of about 20 to 40 Shore A, the housing portion having a first wall and a second wall defining a hollow cavity therebetween, the first wall being structured to engage a portion of the patient, and the mounting portion being structured to couple the outer casing to the support member, the mounting portion having a first side and an opposite second side, wherein the first side and the second side form an internal edge of the mounting portion defining an opening through the mounting portion, wherein the second wall of the housing portion is directly coupled to and extends directly from the second side of the mounting portion at the internal edge, and wherein the first side of the mounting portion comprises a coupling mechanism extending therefrom in a direction away from the housing portion, the coupling mechanism being structured to couple the pad assembly to the support member, and
a support element disposed substantially within the cavity of the outer casing, wherein the opening is structured to flex and receive the support element therethrough for disposing the support element in the cavity by flexing of the mounting portion.

7. The patient interface device of claim 6, wherein the first wall of the housing portion is generally curved and wherein the second wall of the housing portion is generally curved a greater amount than the first wall.

8. The patient interface device of claim 6, wherein the support element comprises an open cell foam material.

9. The patient interface device of claim 6, wherein the support element comprises a closed cell foam material.

10. The patient interface device of claim 6, wherein the outer casing is formed from a silicone or thermoplastic elastomer material.

11. A method of providing a customizable pad assembly for use with a patient interface device for delivering a flow of gas to an airway of a patient, the method comprising:
providing an outer casing having a housing portion and a mounting portion formed as a unitary member made of a flexible material having a hardness of about 20 to 40 Shore A, the housing portion having a first wall and a second wall defining a hollow cavity therebetween, the first wall being structured to engage a portion of the patient, and the mounting portion being structured to couple the outer casing to the patient interface device, the mounting portion having a first side and an opposite second side, wherein the first side and the second side form an internal edge of the mounting portion defining an opening through the mounting portion. wherein the second wall of the housing portion is directly coupled to and directly extends from the second side of the mounting portion at the internal edge, and wherein the first side of the mounting portion comprises a coupling mechanism extending therefrom in a direction away from the housing portion, the coupling mechanism being structured to couple the pad assembly to the patient interface device; and
providing a plurality of support elements, each support element being disposable substantially within the cavity of the outer casing, wherein the opening structured to flex and receive each of the support elements therethrough for disposing each of the support elements in the cavity by flexing of the mounting portion.

12. The method of claim 11, wherein providing a plurality of support elements comprises providing a plurality of support elements of varying density.

13. The method of claim 11, wherein providing a plurality of support elements comprises providing a plurality of support elements of varying softness.

* * * * *